United States Patent [19]

Bank et al.

[11] Patent Number: 5,567,837
[45] Date of Patent: Oct. 22, 1996

[54] DISUBSTITUTED PALLADIUM CATALYSTS FOR REACTING ORGANIC HALIDES WITH DISILANES

[75] Inventors: Howard M. Bank, Freeland; Brian M. Naasz, DeWitt; Binh T. Nguyen, Midland, all of Mich.

[73] Assignee: Dow Corning Corporation, Midland, Mich.

[21] Appl. No.: 593,317

[22] Filed: Jan. 31, 1996

[51] Int. Cl.⁶ ........................................ C07F 7/08
[52] U.S. Cl. ........................................ 556/468
[58] Field of Search ........................ 556/468

[56] References Cited

U.S. PATENT DOCUMENTS

| | | | |
|---|---|---|---|
| 2,598,434 | 5/1952 | Mohler et al. | 556/468 |
| 2,709,176 | 5/1955 | Bluestein | 556/468 |
| 2,837,552 | 6/1958 | George et al. | 556/468 |
| 3,772,347 | 11/1973 | Atwell et al. | 260/448.2 E |
| 4,461,908 | 7/1984 | Takamizawa et al. | 556/468 X |
| 4,962,219 | 10/1990 | Halm et al. | 556/468 |
| 5,292,909 | 3/1994 | Chadwick et al. | 556/468 |
| 5,292,912 | 3/1994 | Chadwick et al. | 556/468 |
| 5,326,896 | 7/1994 | Chadwick et al. | 556/468 X |

OTHER PUBLICATIONS

Eaborn et al., J. Organometallic Chem. 225:331–341 (1982).

*Primary Examiner*—Paul F. Shaver
*Attorney, Agent, or Firm*—William F. Boley

[57] ABSTRACT

A process for reacting organic halides with disilanes to form monosilanes. The process uses disubstituted palladium compounds as catalysts. The process is especially useful for reacting alkenyl chlorides, such as allyl chloride, with disilanes to form monosilanes having alkenyl substitution. The process is also useful for converting the high-boiling disilane containing fraction resulting from the direct process for forming organosilanes into more useful monosilanes.

17 Claims, No Drawings

DISUBSTITUTED PALLADIUM CATALYSTS FOR REACTING ORGANIC HALIDES WITH DISILANES

BACKGROUND OF INVENTION

The present invention is a process for reacting organic halides with disilanes to form monosilanes. The process uses disubstituted palladium compounds as catalysts. The process is especially useful for reacting alkenyl chlorides, such as allyl chloride, with disilanes to form monosilanes having alkenyl substitution. The process is also useful for converting the high-boiling disilane containing fraction resulting from the direct process for forming organosilanes into more useful monosilanes.

The primary commercial method for producing organosilanes involves the reaction of an organic halide with elemental silicon. After the desired organosilanes have been recovered from the product mixture by distillation there remains a high-boiling residue which comprises among other components disilanes. Since these disilanes have very little commercial value it is desirable to convert them to the more useful monosilanes. The present invention relates to a process for converting disilanes to monosilanes by contacting the disilanes with and organic halide in the presence of a disubstituted palladium catalyst. In the process the Si—Si bond of the disilane is broken resulting in the formation of two monosilanes, with the organic group of the organic halide substituting on one of the silicon atoms and the halogen group of the organic halide substituting on the other silicon atom.

Atwell et al., U.S. Pat. No. 3,772,347, describe the use of palladium/phosphine compounds as catalysts for the reaction of disilanes and organic halides to form monosilanes. Atwell et al. teach such catalyst are useful, for example, for the reaction of hexachlorodisilane with allyl chloride to give allyltrichlorosilane.

Eaborn et al., J. Organometallic Chem. 225:331–341 (1982) describe the reactions of a range of organic halides with hexamethyldisilane or hexachlorodisilane in toluene in the presence of a palladium catalyst containing phosphine ligands.

SUMMARY OF INVENTION

The present invention is a process for reacting organic halides with disilanes to form monosilanes. The process uses disubstituted palladium compounds as catalysts. The process is especially useful for reacting alkenyl chlorides, such as allyl chloride, with disilanes to form monosilanes having alkenyl substitution. The process is also useful for converting the high-boiling disilane containing fraction resulting from the direct process for forming organosilanes into more useful monosilanes.

DESCRIPTION OF INVENTION

The present invention is a process for forming monosilanes from disilanes. The process comprises contacting a mixture comprising a disilane described by formula

and an organic halide described by formula $R^1X$ with a disubstituted palladium catalyst described by formula

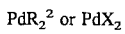

at a temperature within a range of about 100° C. to 250° C., where each $R^1$ is an independently selected monovalent hydrocarbon radical comprising about one to 18 carbon atoms, each $R^2$ is an independently selected monovalent radical selected from a group consisting of saturated linear and saturated branched monovalent hydrocarbon radicals comprising about one to 18 carbons atoms, aryls, and oxo carboxyls; each X is independently selected from a group consisting of chlorine and bromine atoms, and n=0 to 6.

Contact of the mixture with the disubstituted palladium catalyst can be effected in any standard pressurizable reactor suitable for contact with halosilanes. The process may be run as a batch, semi-continuous, or continuous process.

The mixture of the present process comprises disilanes described by formula $R_n^1 Si_2Cl_{6-n}$, where each $R^1$ is an independently selected monovalent hydrocarbon radical comprising about one to 18 carbon atoms and n=0 to 6. $R^1$ can be, for example, an alkyl such as methyl, ethyl, propyl, and tert-butyl; cycloalkyl such as cyclopentyl and cyclohexyl; an alkenyl such as vinyl, allyl, and hexenyl; an aryl such as phenyl, tolyl, and naphthyl. Preferred is when $R^1$ is methyl. The value n can be any value from zero to six. It is preferred that n be a value within a range of two to six. Most preferred is when n is six. A preferred disilane for use in the present process is hexamethyldisilane. The present process can be used to convert a mixture of disilanes as described by the above formula into monosilanes.

The present process is useful for converting a high-boiling disilane containing fraction resulting from the reaction of an organic halide with elemental silicon to useful monosilanes. In a typical process for reacting an organic halide with elemental silicon, the process is conducted at a temperature of about 300° C. to 350° C. in the presence of suitable catalysts and gaseous product and feed compounds along with fine particulates are continuously removed from the process. The removed materials are subsequently distilled to recover monosilanes, leaving a "high-boiling fraction." A preferred high-boiling fraction for use in the present process is one with a boiling point above about 70° C. resulting from the distillation of monosilanes from the reaction product of methyl chloride with elemental silicon. A typical composition for such a high-boiling fraction comprises about 50–60 weight percent disilanes. The composition of a high-boiling fraction useful in the present process is described, for example, in Ferguson et al., U.S. Pat. No. 5,430,168, which is incorporated by reference for its teaching of such compositions. In some instances, it may be desirable to pre-treat the high-boiling fraction by a process such as filtration to remove particulates.

In addition to the disilanes, the mixture of the present process comprises an organic halide described by formula $R^1X$, where $R^1$ is as described above and X is a bromine or chlorine atom. It is preferred that the $R^1$ substituent of the organic halide be an alkenyl radical. It is preferred that X be chlorine. The preferred organic halide for use in the present process is allyl chloride.

The mole ratio of organic halide to disilane is not critical to the present process and can be varied from about 0.1:1 to 10:1. However, it is preferred that the mole ratio of organic halide to disilane be at least 1:1. Even more preferred is when the organic halide is present in the process in slight to moderate stoichiometric excess, that is within a range of greater than 1:1 to about 3:1.

The mixture comprising the disilane and organic halide is contacted with a disubstituted palladium catalyst described by formula $PdR_2^2$ or $PdX_2$, where each $R^2$ is an independently selected monovalent radical selected from a group consisting of saturated linear and saturated branched monovalent hydrocarbon radicals comprising about one to 18 carbon atoms, aryls, and oxo carboxyls and each X is independently selected from a group consisting of chlorine and bromine atoms. $R^2$ can be for example an alkyl such as methyl, ethyl, propyl, tert-butyl, and hexyl; a cycloalkyl such as cyclopentyl and cyclohexyl; an aryl such as phenyl, tolyl, and naphthyl; and an oxo carboxyl such as glyoxyloyl, pyruvoyl, and acetoacetyl. Preferred is when $R^2$ is acetoacetyl. Preferred is when X is chlorine atoms. A preferred disubstituted palladium catalyst is selected from a group consisting of palladium dichloride and bis-acetoacetyl palladium.

The concentration of the catalyst in the present process, based upon the weight of elemental palladium, can be within a range of about 10 ppm to $2 \times 10^5$ ppm palladium, based upon weight of the mixture. Preferred is when the concentration of catalyst in the process, is within a range of about 100 ppm to 10,000 ppm palladium on the same basis. Most preferred is when the concentration of catalyst is within a range of 100 ppm to 1,000 ppm palladium on the same basis.

The present process can be conducted at a temperature within a range of about 100° C. to 250° C. Preferred is when the process is conducted at a temperature within a range of about 150° C. to 200° C.

The following examples are provided to illustrate the present invention. These examples are not intended to limit the scope of the claims herein.

The reactions reported in the examples were conducted in sealed pyrex glass tubes. A reaction mixture as described in each example was placed in the glass tube and cooled in a IPA/dry ice bath. The tube was then heat sealed and heated at the temperature and for the time described for each example. At the end of the described reaction period the content of the tube was cooled and analyzed by gas chromatography using a flame ionization detector (GC-FID). The results are reported as the area percent (area %) under the GC-FID trace. In the formulas of the examples, Me is methyl and AcAc is acetoacetyl.

Example 1 (Reference example)

The reaction mixture comprised 0.43 g (0.003 mol) of $Me_3SiSiMe_3$ and 0.3 g (0.0039 mol) of allyl chloride. The mixture was heated at 150° C. for 21 hours, then cooled and analyzed by GC-FID. The analysis indicated the presence of 12 area % $Me_3SiSiMe_3$, 12 area % allyl chloride, 47 area % allylSiMe$_3$, and 25 area % Me$_3$SiCl.

Example 2

The reaction mixture comprised 0.43 g of $Me_3SiSiMe_3$, 0.3 g of allyl chloride, and 0.003 g of $Pd(AcAc)_2$. The mixture was heated at 150° C. for 21 hours, then cooled and analyzed by GC-FID. The analysis indicated the presence of no $Me_3SiSiMe_3$, 4.8 area % allyl chloride, 59.3 area % allylSiMe$_3$, and 31.3 area % Me$_3$SiCl.

Example 3

The reaction mixture comprised 0.43 g of $Me_3SiSiMe_3$, 0.3 g of allyl chloride, and 0.004 g of $PdCl_2$. The mixture was heated at 150° C. for 21 hours, then cooled and analyzed by GC-FID. The analysis indicated the presence of no $Me_3SiSiMe_3$, 3.5 area % allyl chloride, 60.2 area % allyl-SiMe3. and 31.9 area % Me$_3$SiCl.

Example 4 (Reference example)

The reaction mixture comprised 0.56 g (0.003 mol) of $Me_3SiSiMeCl_2$ and 0.3 g (0.0039 mol) of allyl chloride. The mixture was heated at 150° C. for 48 hours, then cooled and analyzed by GC-FID. The analysis showed no reaction had occurred.

Example 5

The reaction mixture comprised 0.56 g of $Me_3SiSiMeCl_2$, 0.3 g of allyl chloride, and 0.0026 g of $Pd(AcAc)_2$ The mixture was heated at 150° C. for 15 hours, then cooled and analyzed by GC-FID. The analysis indicated the presence of no $Me_3SiSiMeCl_2$, 10.2 area % allyl chloride, 41.7 area % allylSiMeCl$_2$, 38.3 area % Me3SiCl, and 0.8 area % allyl-SiMe$_3$.

Example 6 (Reference example)

The reaction mixture comprised 0.68 g (0.003 mol) of $Cl_2MeSiSiMeC_2$ and 0.3 g (0.0039 mol) of allyl chloride. The mixture was heated at 200° C. for 17 hours, then cooled and analyzed by GC-FID. The analysis indicated the presence of 17.2 area % $Cl_2MeSiSiMeCl_2$, 20.2 area % allyl chloride, 31.9 area % allylSiMeCl$_2$, and 12 area % of MeSiCl$_3$.

Example 7

The reaction mixture comprised 0.68 g of $Cl_2MeSiSiMeCl_2$, 0.3 g of allyl chloride, and 0.0035 g of $PdCl_2$. The mixture was heated at 200° C. for 17 hours, then cooled and analyzed by GC-FID. The analysis indicated the presence of no $MeCl_2SiSiMeCl_2$, 0.4 area % allyl chloride, 48 area % allylSiMeCl$_2$, and 25 area % MeSiCl$_3$.

Example 8

The reaction mixture comprised 0.68 g of $Cl_2MeSiSiMeCl_2$, 0.3 g of allyl chloride, and 0.0032 g of $Pd(AcAc)_2$. The mixture was heated at 200° C. for 17 hours, then cooled and analyzed by GC-FID. The analysis indicated the presence no $Cl_2MeSiSiMeCl_2$, 3.7 area % allyl chloride, 50 area % allylSiMeCl$_2$, and 23 area % MeSiCl$_3$.

Example 9 (Reference example)

The reaction mixture comprised 0.55 g of a high-boiling (>70° C.) distillation fraction resulting from the reaction of methyl chloride with elemental silicon and 0.3 g (0.0039 mol) of allyl chloride. Major disilane components present in the high-boiling fraction as determined by GC-FID were 24.7 area % $Cl_2MeSiSiMeCl_2$, 25.4 area percent $Me_2ClSiSiMeCl_2$, 11.6 area % $Me_2ClSiSiMe_2Cl$, and 2.8 area % $Me_3SiSiMeCl_2$. The mixture was heated at 200° C. for 17 hours, then cooled and analyzed by GC-FID. The analysis indicated the presence of 6 area % disilanes, 19.6 area % allyl chloride, 23 area % allylSiCl$_2$Me, and 5.9 area % of allylSiMe$_2$Cl.

Example 10

The reaction mixture comprised 0.55 g of a high-boiling fraction as described in Example 10, 0.3 g of allyl chloride, and 0.0038 g of $Pd(AcAc)_2$. The mixture was heated at 200° C. for 17 hours, then cooled and analyzed by GC-FID. The analysis indicated the presence of no disilane, 1.2 area % allyl chloride, 16 area % allylSiMeCl$_2$, and 1.2 area % allylSiMe$_2$Cl.

Example 11

The reaction mixture comprised 0.55 g of a high-boiling fraction as described in Example 10, 0.3 g of allyl chloride, and 0.0038 g of $PdCl_2$. The mixture was heated at 200° C. for 17 hours, then cooled and analyzed by GC-FID. The analysis indicated the presence of no disilane, no area % allyl chloride, 18 area % allylSiMeCl$_2$, and 1 area % allylSiMe$_2$Cl.

We claim:

1. A process for forming monosilanes from disilanes, the process comprising contacting a mixture comprising a disilane described by formula $$R_n^1Si_2Cl_{6-n}$$

and an organic halide described by formula $$R^1X$$

with a disubstituted palladium catalyst described by formula $$PdR_2^2 \text{ or } PdX_2$$

at a temperature within a range of about 100° C. to 250° C., where each $R^1$ is an independently selected monovalent hydrocarbon radical comprising about one to 18 carbon atoms, each $R^2$ is an independently selected monovalent radical selected from a group consisting of saturated linear and saturated branched hydrocarbon radicals comprising about one to 18 carbons atoms, aryls, and oxo carboxyls; each X is independently selected from a group consisting of chlorine and bromine atoms, and n=0 to 6.

2. A process according to claim 1, where the $R^1$ substituents of the disilane are methyl.

3. A process according to claim 1, where n is a value within a range of two to six.

4. A process according to claim 1, where the disilane is hexamethyldisilane.

5. A process according to claim 1, where the mixture comprises a high-boiling fraction resulting from the distillation of monosilanes from the reaction product of methyl chloride with elemental silicon where the high-boiling fraction contains the disilane.

6. A process according to claim 1, where the $R^1$ substituent of the organic halide is an alkenyl radical.

7. A process according to claim 1, where the X substituent of the organic halide is chlorine.

8. A process according to claim 1, where the organic halide is allyl chloride.

9. A process according to claim 1, where the mole ratio of organic halide to disilane in the mixture is within a range of about 0.1:1 to 10:1.

10. A process according to claim 1, where the mole ratio of organic halide to disilane in the mixture is within a range of greater than 1:1 to about 3:1.

11. A process according to claim 1, where the disubstituted palladium catalyst is selected from a group consisting of palladium dichloride and bis-acetoacetyl palladium.

12. A process according to claim 1, where the concentration of palladium in the mixture is within a range of about 10 ppm to $2\times10^5$ ppm.

13. A process according to claim 1, where the concentration of palladium in the mixture is within a range of about 100 ppm to 10,000 ppm.

14. A process according to claim 1, where the concentration of palladium in the mixture is within a range of about 100 ppm to 1,000 ppm.

15. A process according to claim 1, where the temperature is within a range of about 150° C. to 200° C.

16. A process according to claim 1, where the disilane is hexamethyldisilane, the organic halide is allyl chloride, the mole ratio of organic halide to disilane in the mixture is within a range of greater than 1:1 to about 3:1, the disubstituted palladium catalyst is selected from a group consisting of palladium dichloride and bis-acetoacetyl palladium, the concentration of palladium in the mixture is within a range of about 100 ppm to 1,000 ppm, and the temperature is within a range of about 150° C. to 200° C.

17. A process according to claim 1, where the mixture comprises a high-boiling fraction resulting from the distillation of monosilanes from the reaction product of methyl chloride with elemental silicon where the high-boiling fraction contains the disilane, the organic halide is allyl chloride, the mole ratio of organic halide to disilane in the mixture is within a range of greater than 1:1 to 3:1, the disubstituted palladium catalyst is selected from a group consisting of palladium dichloride and bisacetoacetyl palladium, the concentration of palladium in the mixture is within a range of about 100 ppm to 1,000 ppm, and the temperature is within a range of about 150° C. to 200° C.

* * * * *